United States Patent [19]
Jones

[11] Patent Number: 5,924,985
[45] Date of Patent: Jul. 20, 1999

[54] PATIENT PROBE DISCONNECT ALARM

[75] Inventor: Thomas C. Jones, Columbia, Md.

[73] Assignee: Ohmeda Inc., Liberty Corner, N.J.

[21] Appl. No.: 08/902,043

[22] Filed: Jul. 29, 1997

[51] Int. Cl.⁶ .................................................. A61B 5/04
[52] U.S. Cl. ........................ 600/390; 600/534; 600/587
[58] Field of Search ................................ 600/390, 391, 600/392, 393, 534, 587, 549

[56] References Cited

U.S. PATENT DOCUMENTS

| | | |
|---|---|---|
| 3,367,323 | 2/1968 | Schuler . |
| 3,640,270 | 2/1972 | Hoffmann . |
| 4,174,955 | 11/1979 | Blackmer et al. . |
| 4,369,793 | 1/1983 | Staver et al. . |
| 4,537,197 | 8/1985 | Hulka . |
| 4,646,747 | 3/1987 | Lundback . |
| 4,686,995 | 8/1987 | Fournial et al. .......................... 600/391 |
| 4,736,749 | 4/1988 | Lundback . |
| 4,771,784 | 9/1988 | Kozin et al. . |
| 4,895,162 | 1/1990 | Dolliver .................................... 600/534 |
| 5,109,849 | 5/1992 | Goodman et al. . |
| 5,184,858 | 2/1993 | Arai . |
| 5,345,935 | 9/1994 | Hirsch et al. . |

*Primary Examiner*—Max Hindenburg
*Assistant Examiner*—Pamela L. Wingood
*Attorney, Agent, or Firm*—Roger M. Rathbun

[57] ABSTRACT

A patient probe disconnect alarm where the patient probe is provided with a vacuum that is formed in a chamber between the patient probe and the skin of the infant. The level of vacuum is monitored within the chamber and whenever the level of vacuum lessens beyond a predetermined vacuum level, the monitor senses a probe disconnect and provides an alert to the user that there is a loss of integrity in the probe affixation to the infant.

10 Claims, 3 Drawing Sheets

PATIENT PROBE DISCONNECT ALARM

BACKGROUND

This invention relates to noninvasive probes for monitoring the condition of a patient and to a system for sensing when the probe has become disconnected from the patient.

In various medical fields, it is common to have one or more probes that are attached to the skin of a patient. In most cases of real time monitoring, it is relatively easy for the user to determine when the probe has become disconnected from the patient as the signal being monitored generally will either be discontinued or be so unlike the anticipated signal that the user will immediately know that something is wrong. For example, when a EKG probe becomes disconnected from the patient, the loss of a signal becomes readily apparent and the user can take immediate action to reestablish the probe onto the patient.

In the case of infant warmers, however, as an example, generally temperature probes are connected to an infant and which monitor the temperature of that infant. The probe may simply monitor temperature or, as is common, the probe may be used as a feedback loop to control the energy to a heater to provide the amount of heat actually needed by the infant.

In such cases, however, the surrounding temperature may not be that different from the patient temperature so that a patient probe may become disconnected and the user may not see a rapid loss or deterioration of signal or other indication that would provide an early warning of the patient disconnect. Accordingly, the temperature probe for an infant may be disconnected and thus the control of the energy to the heater lost for a period of time that the user is simply unaware of the problem.

Examples of such a patient disconnect devices are shown and described in U.S. Pat. Nos. 4,399,823 and 4,399,824 of Air Shields, Inc., however, the similar systems therein described utilize a precise pulse of heat to the temperature responsive device and the accurate measurement of the dissipation of that heat to determine whether or not the probe is still attached to the patient. That system is somewhat expensive and may not respond as reliably as desired.

Accordingly, it would be advantageous to provide a rapid, yet inexpensive, indicator of a patient disconnect in the use of an infant warmer or other infant control apparatus, such as a incubator where temperature is being monitored and yet which is of sufficient reliability.

SUMMARY OF THE INVENTION

The patient probe of the present invention provides an inexpensive, yet reliable solution to the aforesaid problem. In the present invention, a patient probe includes a slight vacuum that is transmitted from a source of vacuum to the very end of the probe that is attached to the patient. The source of vacuum may be by a regulated source, such as the normal hospital piping system or may be a bellows that is compressed and which maintains the vacuum at the infant probe end. In either case, it is preferred that the level of vacuum be extremely low and not necessarily used for affixing the probe to the patient, although it could be used for such purpose or to supplement other means of affixing the probe to the patient.

In the preferred embodiment, the patient probe is used with an infant care apparatus to monitor the integrity of a temperature probe affixed to the infant. The level of vacuum is continually monitored by a vacuum gauge or vacuum switch and when the level of vacuum set by the switch is no longer maintained, the switch activates an alarm to alert the user that there is a problem with the affixation of the patient probe to the patient's skin.

With the present invention, therefore, the overall components are used and are relatively inexpensive yet all are commercially available components with good reliability.

DETAILED DESCRIPTION OF THE INVENTION

Figure 1:
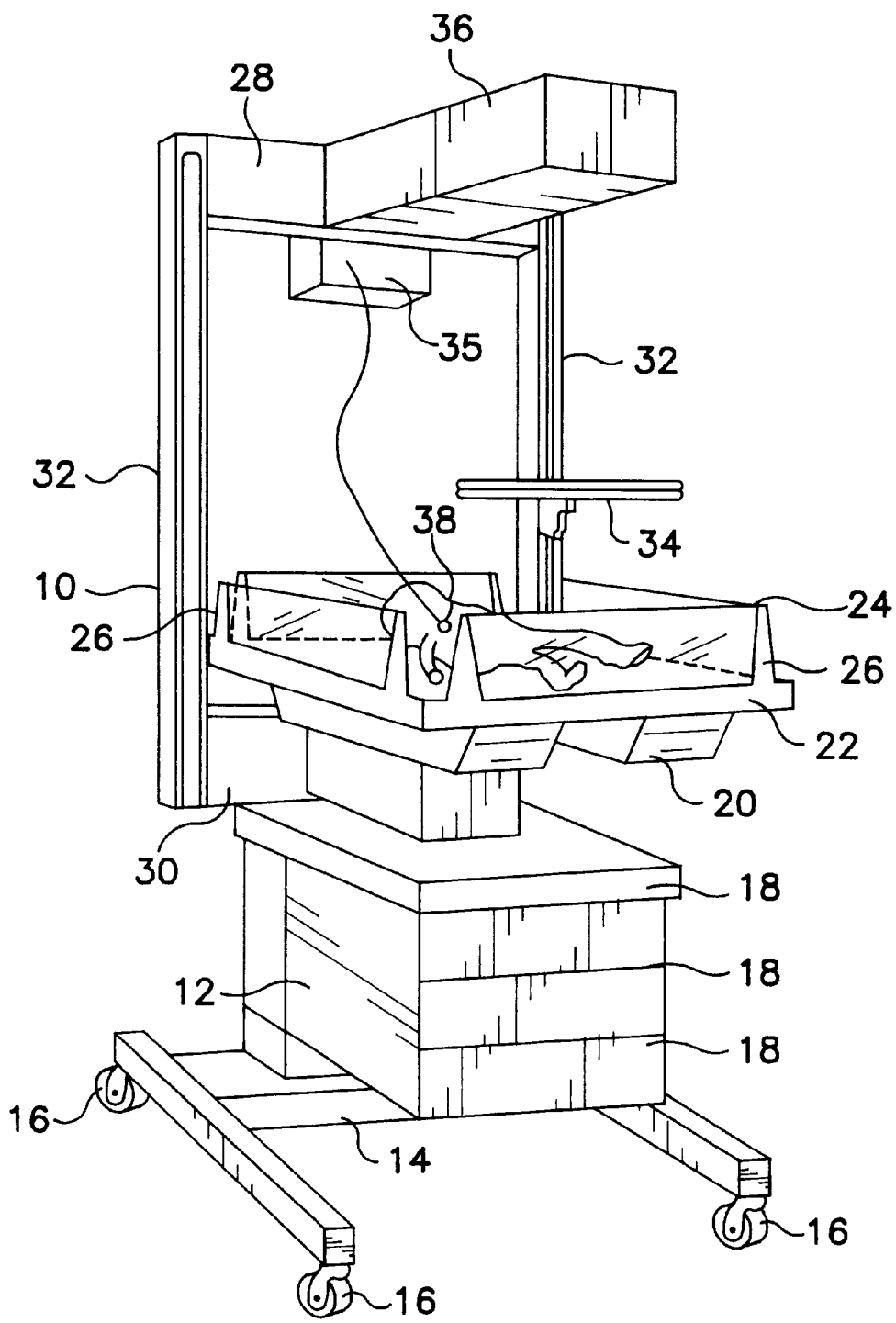
FIG. 1 is an isometric view of an infant care center having a heater and a patient temperature probe usable with the present invention.

Referring now to FIG. 1, there is shown an isometric view of an infant care center having for which the present patient probe disconnect means can be used. As will be noted, however, the present invention can be used with a variety of probes and with a variety of temperature probes used in infant care apparatus, including infant incubators. As shown, the care center includes a frame 10 which provides a free standing unit for the infant care center. The frame 10 is supported upon a cabinet 12 which, in turn, is mounted upon a base 14 having wheels 16 so that the care center is easily movable. The cabinet 12 may also include one or more drawers 18 for containing items for attending to the infant.

An infant pedestal 20 is mounted atop of the cabinet 12 and on which is located an infant bed 22 which underlies an infant positioned thereon. Pedestal 20 is the main support for infant bed 20. The infant bed 22 has a generally planar upper surface 24 with appropriate cushioning material for comfort of the infant and further may be surrounded by guards 26, generally of a clear plastic material, and which contain the infant on the upper surface 24. Generally, the guards 26 are removable and/or releasable for complete access to the infant.

Frame 10 includes upper and lower cross members 28 and 30, respectively, joining a pair of vertical struts 32 and which vertical struts 32 may provide a means of support for other structural parts such as a shelf 34.

Mounted on the upper cross member 28 may be a control module 35 for containing the various electrical controls to operate the care center. In addition, a heater 36 is mounted to the upper cross member 28. As will be noted, the location of the heater 36 is such to be above the infant bed 22. The heater is focused so as to provide a footprint on and around the infant to optimize the amount of heat directed upon the infant. Various types of focusable heaters are available for such application, examples of which may be a Calrod focused heater of about 500–600 watts.

A patient probe 38 is shown for affixation to an infant and is connected to the control module 35 by means such as a plug to make electrical connection thereto. As is conventional, the patient probe 38 continually senses the temperature of the infant contained within the infant care center and that temperature is used, preferably, to control the intensity of the heater 36.

Figure 2:
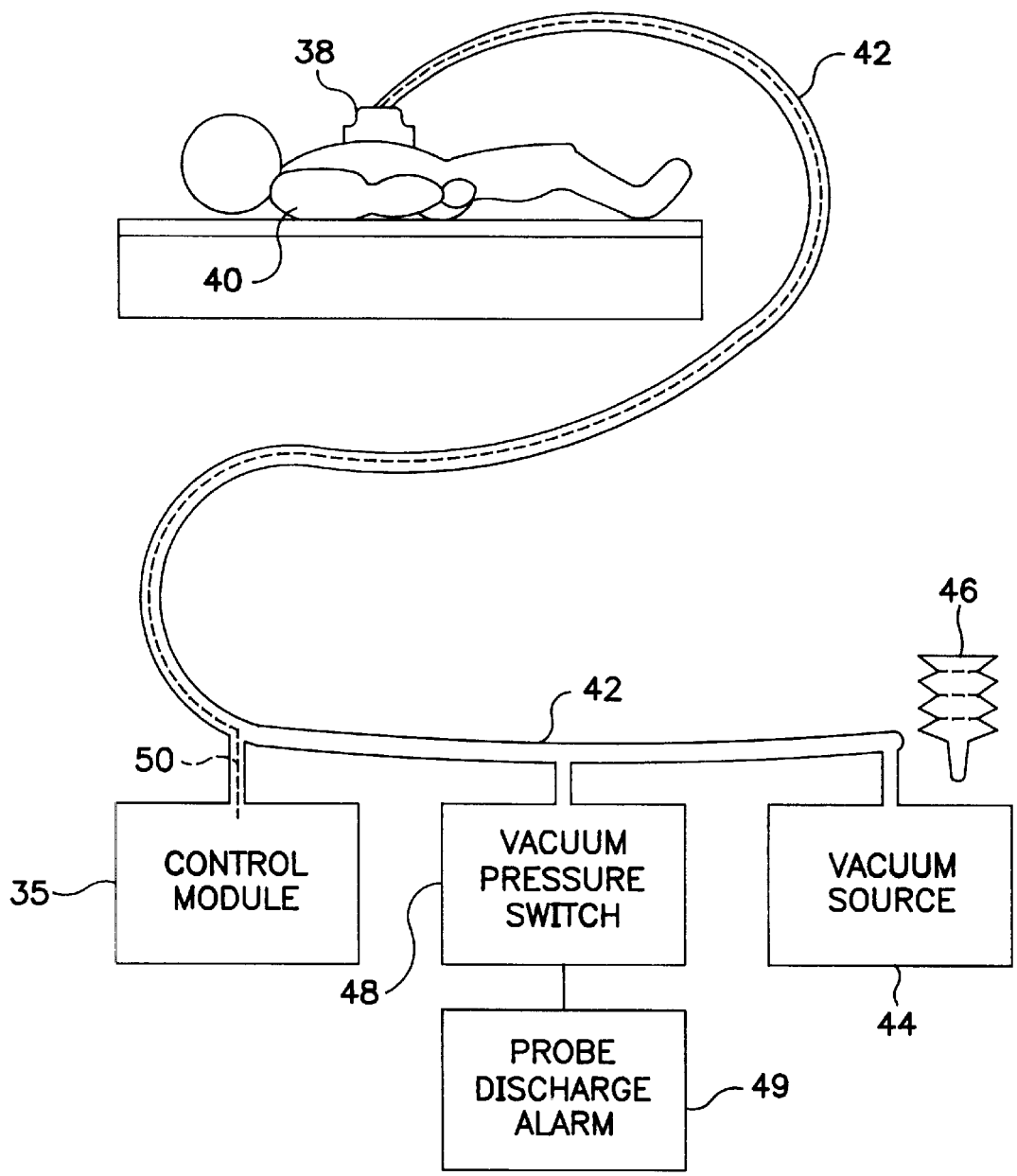
FIG. 2 is a schematic view of the temperature probe disconnect means of the present invention.

Turning now to FIG. 2, there is shown a schematic of an infant care center containing an infant 40 and which incorporates the probe disconnect means of the present invention.

Generally, the patient probe 38 is shown affixed to the infant 40 and such affixation may be through the use of a mild adhesive or seal and or may be by the use of tape. As will be seen, the use of the present invention may also aid in retaining the patient probe 38 onto the infant 40, however that is not the main intent of the present invention.

A pneumatic conduit 42 extends from the patient probe 38 outwardly and is connected to a vacuum source 44. The pneumatic conduit is sealed and contains a column of air that is continually at a negative pressure maintained by the vacuum source 44. The vacuum source may be a regulated source that is derived from the normal hospital vacuum piping system, from a vacuum pump or may be by means of a flexible chamber such as a compressible bellows 46 shown schematically and not connected to the system.

The level of vacuum, in any case, is relatively mild due to the possible effect on the extremely thin skin of the infant 40. As such, the level of vacuum is not intended to be the means of holding the patient probe 38 to the infant, however, it may add some additional negative force in maintaining the patient probe 38 affixed to the infant 40. A vacuum switch 48 is used as the means of continually monitoring the level of vacuum within the pneumatic conduit 42 is set or designed to close when the level of vacuum rises to a predetermined level, indicating that there is a loss of integrity in the pneumatic conduit 42 and thus, likely that the patient probe 38 has become disconnected from the infant 40.

That vacuum source 48 can then be used to activate an alarm 50 to alert the user or attending personnel that there is a problem with the affixation of the patient probe 38 to the infant 40 at an early instance. The electrical wires 50 used to connect the patient probe 38 to the control module 35 are also shown and may be carried within the pneumatic conduit 42 for a certain length and then brought out in a sealed arrangement.

Figure 3:
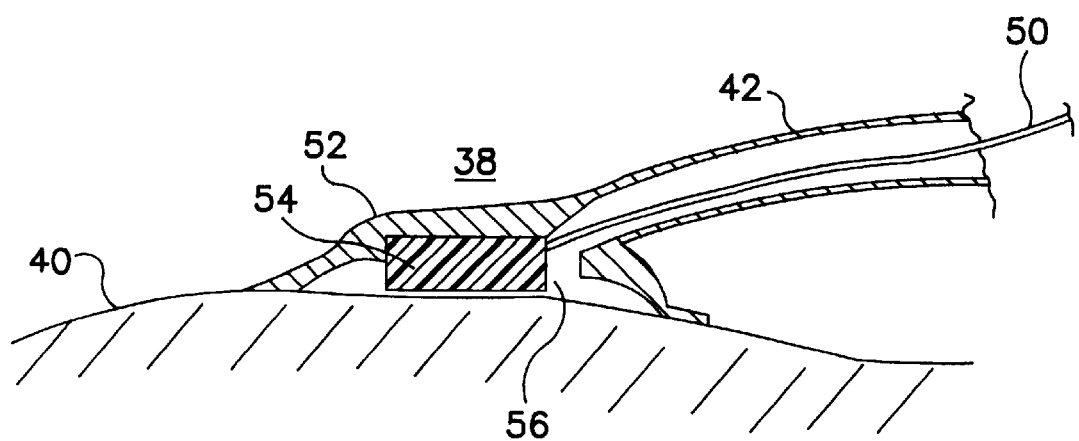
FIG. 3 is a schematic view of the details of one of he components of the patient disconnect means of the present invention.

Turning now to FIG. 3, there is shown a further schematic showing the components of the patient probe 38 utilizing the present invention. The patient probe 38 is held to the skin of the infant 40 by, for example, a mild adhesive or the normal medical tape. Patient probe 38 comprises a probe body 52 that is, of course, sealed to the infant 40 and which holds a temperature sensor 54 against the skin of the infant 40. Since the probe body 52 can be made larger than the temperature sensor 54, there is formed, a chamber 56 that surrounds the temperature sensor 54. The pneumatic conduit 42 communicates the vacuum to the chamber 56 and is a part of the sealed system that includes the chamber 56, the pneumatic conduit 42 and back to the vacuum source 44.

As shown, the chamber is an annular chamber 54 that surrounds the temperature sensor 54, however, since the use of the vacuum is not to be the main affixing means of the patient probe 38 to the infant 40, the chamber 56 may be considerably smaller and may even be only the end of the pneumatic conduit 42 acting against the skin of the infant 40. Again, the electrical wires 50 that carry the sensed signal representing the temperature of the infant 40 to the control module are shown and may, or may not, be within the pneumatic conduit 42.

While the present invention has been set forth in terms of a specific embodiment, it will be understood that the patient probe disconnect detection system herein disclosed may be modified or altered by those skilled in the art t other configurations. Accordingly, the invention is to be broadly construed and limited only by the scope and spirit of he claims appended hereto.

I claim:

1. A patient probe disconnect warning system for an infant apparatus, said system comprising;

a patient probe adapted to be affixed to the skin of an infant, said patient probe forming a closed chamber against the skin of the infant, means to draw a vacuum within said closed chamber;

means to monitor the level of vacuum drawn in said chamber, a sensor adapted to determine when the level of vacuum monitored by the monitoring means raises above a predetermined level, and alarm means adapted to alert the user when the vacuum has risen to the level sensed by said sensor.

2. A patient probe disconnect warning system for an infant apparatus as defined in claim 1 wherein said means to draw a vacuum comprises a collapsible bellows.

3. A patient probe disconnect warning system for an infant apparatus as defined in claim 1 wherein said sensor comprises a vacuum switch.

4. A patient probe disconnect warning system for an infant apparatus as defined in claim 1 wherein said patient probe includes a heat sensor.

5. An infant care apparatus for providing heat to an infant, said infant care apparatus comprising;

a heater to provide heat to the infant;

a patient probe adapted to be affixed to the skin of the infant, said patient probe comprising a temperature sensor adapted to sense the temperature of the skin of the infant, said probe further forming a closed chamber between said probe and the skin of the infant, vacuum means to draw a vacuum in said chamber, monitoring means to monitor the level of vacuum drawn in said closed chamber alarm means adapted to alert the user when the level of vacuum monitored by said monitoring means lessens to a level above a predetermined vacuum level.

6. An infant care apparatus for providing heat to an infant as defined in claim 5 wherein said temperature sensor controls said heater.

7. An infant care apparatus for providing heat to an infant as defined in claim 5 wherein said closed chamber is annular and surrounds said temperature sensor.

8. An infant care apparatus for providing heat to an infant as defined in claim 5 wherein said source of vacuum comprises a collapsible bellows.

9. Vacuum in chamber aids if maintaining the probe affixed to the infant as defined in claim 5 wherein said vacuum source is a hospital regulated supply of vacuum.

10. A method of sensing the disconnection of a patient probe for determining the skin temperature of a patient, said method comprising the steps of:

providing a patient probe for affixation to a patient;

affixing the patient probe to a patient;

forming a chamber between the patient probe and the skin of the patient;

maintaining a vacuum in said chamber monitoring the level of vacuum in the chamber triggering an alarm when the level of vacuum increases to a level higher than a predetermined vacuum limit.

* * * * *